(12) United States Patent
Lin (10) Patent No.: US 10,010,358 B2
(45) Date of Patent: Jul. 3, 2018

(54) INTERNAL FIXATION PLATE FOR STERNOCLAVICULAR JOINT

(71) Applicant: Lie Lin, Linhai (CN)

(72) Inventor: Lie Lin, Linhai (CN)

( * ) Notice: Subject to any disclaimer, the term of this patent is extended or adjusted under 35 U.S.C. 154(b) by 271 days.

(21) Appl. No.: 15/055,645

(22) Filed: Feb. 29, 2016

(65) Prior Publication Data
US 2017/0189088 A1    Jul. 6, 2017

(30) Foreign Application Priority Data
Dec. 31, 2015 (CN) .......................... 2015 1 1027355

(51) Int. Cl.
*A61B 17/80* (2006.01)
(52) U.S. Cl.
CPC ................................ *A61B 17/8076* (2013.01)
(58) Field of Classification Search
CPC ........................ A61B 17/8076; A61B 17/8033
See application file for complete search history.

(56) References Cited

U.S. PATENT DOCUMENTS

| | | | | |
|---|---|---|---|---|
| 4,964,403 A * | 10/1990 | Karas | .................... | A61B 17/746 606/291 |
| 5,674,222 A * | 10/1997 | Berger | .................. | A61B 17/746 606/284 |
| 7,951,176 B2 * | 5/2011 | Grady, Jr. | ............. | A61B 17/746 606/280 |
| 9,517,096 B2 * | 12/2016 | Madjarov | .......... | A61B 17/8076 |
| 9,795,424 B2 * | 10/2017 | Austin | ............... | A61B 17/8033 |

FOREIGN PATENT DOCUMENTS

| CN | 2686545 Y | 3/2005 |
|---|---|---|
| CN | 101028208 A | 9/2007 |
| CN | 201005772 Y | 1/2008 |
| CN | 202044334 U | 11/2011 |
| CN | 102038547 B | 3/2012 |
| CN | 202619831 U | 12/2012 |
| CN | 202950734 U | 5/2013 |
| CN | 203042414 U | 7/2013 |
| CN | 203609557 U | 5/2014 |

* cited by examiner

*Primary Examiner* — Andrew Yang
(74) *Attorney, Agent, or Firm* — Minder Law Group; Willy H. Wong (57) ABSTRACT

An internal fixation plate for sternoclavicular join comprises a locating rod junction and the clavicle fixation segment, both with flat cross sections. The locating rod junction and the clavicle fixation segment are not in the same plane, and the transition segment connects in between the locating rod junction and the clavicle fixation segment. The clavicle fixation segment is of a long strip, and screw holes are designed in the clavicle fixation segment. The locating rod junction is movably connected to the cylindrical sternum locating rod, through the connector, and allows the sternum locating rod to rotate and swing relative to the locating rod junction. The internal fixation plate connects the clavicle fixation segment to the sternum locating rod through a movable connection, so as to prevent the sternum locating rod from scratching and enlarging the bone holes in sternum.

20 Claims, 12 Drawing Sheets

INTERNAL FIXATION PLATE FOR STERNOCLAVICULAR JOINT

RELATED APPLICATIONS

This application claims benefit to Chinese Patent Application No. CN201511027355.0, filed Dec. 31, 2015.

The above applications and all patents, patent applications, articles, books, specifications, other publications, documents, and things referenced herein are hereby incorporated herein in their entirety for all purposes. To the extent of any inconsistency or conflict in the definition or use of a term between any of the incorporated publications, documents, or things and the text of the present document, the definition or use of the term in the present document shall prevail.

BACKGROUND OF THE INVENTION

Field of Invention

The present invention relates to the technical field of medical apparatus, and particularly to an internal fixation plate for sternoclavicular joint.

Related Art

The fracture and dislocation of the sternoclavicular joint is a clinical common and frequently occurring disease, and can even be life-threatening. Because the sternum is a cancellous bone, and the clavicle is located anterolateral to the sternoclavicular joint, Kirschner wires, plates and screws cannot be fixed effectively on the sternum, the effect of intraoperative reposition is bad, and the postoperative dislocation and pain are common. The curative effect is poor.

A prior art sternoclavicular hooking plate has a zigzag structure. One end of the plate is a hook-shaped structure with a round cross section, and the other end is a flat-plated structure. An arc transition is in the middle. The hook-shaped structure and the flat structure are not in the same plane. The hook-shaped structure is similar to "L" shape, and the flat steel plate structure is slightly arc shaped, whose curve adapts to the anterior arc of the proximal segment of clavicle. There are screw holes in the plate. During the operation, drilling of holes on the sternum is required. The hook-shaped structure of the sternoclavicular hooking plate hooks the hole through the posterior bone tissues of sternum. The sternoclavicular joint is repositioned by adjusting the zigzag structure. The flat structure is arranged along the anterior arc of clavicle, and is fixed to the clavicle through screws, so as to reposition the sternum and the clavicle, and maintain the reposition state.

The sternoclavicular hooking plate stated above can achieve the internal fixation of the sternoclavicular joint, and good effect is obtained in clinical applications. However, since the sternoclavicular joint is the only movable joint that connects the upper limb and the trunk, after a long time of clinical application, it is found that, after the patient's operation, the bone holes in sternum get enlarged, and the hooking end displaced to different extent. For some rare patients suffering severe osteoporosis and patients not following doctor's advice, even sternum fractures may occur through bone holes. This results in a failure of internal fixation.

SUMMARY OF THE INVENTION

One objective of a preferred embodiment of the invention is to avoid the issues stated above in the prior art, and to provide an internal fixation plate for sternoclavicular joint.

The technical issue resolved by a preferred embodiment of the invention is to reduce the agitation of the hooking end in the bone hole in sternum, when the clavicle is moving, which enlarges the bone hole or even detaches the hooking end.

The objective can be achieved by the following technical proposal:

An internal fixation plate for sternoclavicular joint comprises a locating rod junction and the clavicle fixation segment, both with flat cross sections. The locating rod junction and the clavicle fixation segment are not in the same plane, and the transition segment connects in between the locating rod junction and the clavicle fixation segment. The clavicle fixation segment is of a long strip. Screw holes are designed in the clavicle fixation segment, wherein the locating rod junction is movably connected to the columnar sternum locating rod, through the connector. This allows the sternum locating rod to rotate or swing relative to the locating rod junction.

During the internal fixation operation, with the internal fixation plate of the sternoclavicular joint, by passing the sternum locating rod through bone holes in sternum from its posterior side and get fixed to sternum, by bending the clavicle fixation segment around the posterior sternum and to the anterior clavicle proximal, and by drilling holes and then securing the clavicle fixation segment onto clavicle with screws, so as to reposition and secure sternum and clavicle, to maintain the reposition of sternoclavicular joint for healing the ligament and fracture, and to allow the sternoclavicular joint to recover its function. The differences between a preferred embodiment of the internal fixation plate of the sternoclavicular joint and the prior art are: the sternum locating rod is movably connected to the locating rod junction. This enables the sternum locating rod and the clavicle fixation segment a movement similar to that of a joint. In the patients' ordinary activities during the convalescence, when a relative movement between the sternum and the clavicle happens, the sternum locating rod can accordingly rotate and swing relative to the locating rod junction, so as to prevent the sternum locating rod from scratching the bone holes in sternum, to prevent the bone holes from enlarging, the sternum locating rod from moving, and to avoid sternal fracture, and to increase the success rate of the internal fixation operation in sternoclavicular joint.

In the internal fixation plate for sternoclavicular joint stated above, on the end of the connector connected with the locating rod junction, there is a movable head with a diameter greater than the connector. There is a circular arc shaped guiding surface on the movable head. There is a connecting hole on the locating rod junction penetrating through the top and bottom surfaces of the locating rod junction, and there is a pilot concave inside the connecting hole, whose shape matches the guiding surface. The guiding surface can press against the pilot concave, as the connector passes through the connecting hole. There is a clearance between the connector and the inner wall of the connecting hole. The other end of the connector is fixed to the sternum locating rod. During the operation, the locating rod of sternum is installed into the bone holes in sternum and is fixed to it. This allows the guiding surface on the connector to fit the pilot concave inside the connecting hole to achieve the reposition of sternum and clavicle. During the postoperative recovery, the normal movements of sternum and clavicle drive the guiding surface on the connector to slide along the pilot concave, and allow the sternum locating rod to slightly rotate and swing relative to the locating rod junction. This reduces the agitation force that the sternum locating rod is subject to, and hence mitigates the scratches between the sternum locating rod and the bone holes, which is beneficial to the postoperative recovery.

As preferred, in the internal fixation plate for sternoclavicular joint stated above, there is a threaded segment on the connector. On the sternum locating rod, there is a threaded hole fitting the threaded segment. On the sternum locating rod, there is a locating pin designed in the radial direction, which can lock the connector onto the sternum locating rod. The sternum locating rod is connected to the connector by means of threaded connection. The distance between the sternum locating rod and locating rod junction can be adjusted, which is convenient for the preoperative preparation and adjustment. The locating pin is designed to penetrate the sternum locating rod, further locking the screw to the sternum locating rod. The locating pin and the screw lock with each other, to avoid parts detaching from their locations to cause a medical accident.

In the internal fixation plate for sternoclavicular joint stated above, one end of the connector is fixed to the locating rod junction. The sternum locating rod is connected to the other end of the connector, through a spherical connecting structure. The connector may be fixed to the locating rod junction by means of riveting or interference fit, etc. facilitating machining in production processes. During the movements of clavicle and sternum, the spherical connecting structure allows the sternum locating rod to rotate and swing relative to the connector, which is beneficial to the patient's postoperative recovery.

In the internal fixation plate for sternoclavicular joint stated above, the spherical connecting structure comprises a ball head on the end of the connector connecting to the sternum locating rod. The end of the sternum locating rod is petaloid, and has a spherical hole fitting the ball head. The ball head is embedded into the spherical hole. The ball head is installed into the spherical hole during the production process. The ball head cannot detach from the spherical hole during use. This ensures the integrity of the internal fixation plate for sternoclavicular joint.

As an alternative proposal, in the internal fixation plate for sternoclavicular joint stated above, the spherical connecting structure comprises a ball head on the end of the connector connecting to the sternum locating rod. On the end of the sternum locating rod connecting to the connector, there is a spherical enclosing cavity. A threaded cover is also screwed onto the sternum locating rod, locating the ball head inside the enclosing cavity. There is a clearance hole on the threaded cover, for the connector to pass through. There is a clearance between the clearance hole and the connector. In the preoperative preparation stage, the threaded cover may be unscrewed. After changing the sternum locating rod with one of appropriate dimensions according to the requirements for the operation, the threaded cover can be screwed back tightly; therefore, it is more convenient to use.

As preferred, in the internal fixation plate for sternoclavicular joint stated above, at the position of the sternum locating rod corresponding to the enclosing cavity, there is a petaloid structure, and the outer wall of the sternum locating rod has a conical surface. The inner wall of the threaded cover has a pilot cone matching the conical surface.

As preferred, in the internal fixation plate for sternoclavicular joint stated above, there are several screw holes. The screw holes are arranged in the lengthwise direction of the clavicle fixation segment, and the screw holes have countersinks and internal screw threads. The cortical bone screw passes through the screw hole and gets screwed tightly onto clavicle, to position the clavicle fixation segment. The head of the cortical bone screw fits the countersink of the screw hole, which avoids the cortical bone screw's loosening. The cortical bone screw does not tend to detach because of the internal screw threads.

As further preferred, in the internal fixation plate for sternoclavicular joint stated above, at the position adjacent to at least one screw hole, there is a locking hole designed with a countersink. The locking hole partially overlaps the screw hole. The provision of the locking hole will satisfy the requirement for internal fixation with increased pressure, and further enhance the fixation effect between the clavicle fixation segment and clavicle.

In the internal fixation plate for sternoclavicular joint stated above, the transition segment comprises a segment proximal to sternum connecting to the locating rod junction, and a segment proximal to clavicle connecting to the clavicle fixation segment. In between the segment proximal to sternum and segment proximal to clavicle is the yielding segment. The curve of the yielding segment makes the segment proximal to sternum and the segment proximal to clavicle staggered in the fore-and-aft direction. The segment proximal to sternum bends relative to the yielding segment and the segment proximal to clavicle bends relative to the yielding segment in the opposite direction, making the segment proximal to sternum and the segment proximal to clavicle staggered in space.

The fore-and-aft stagger between the segment proximal to sternum and the segment proximal to clavicle caused by the yielding segment, allows that, in the postoperative activities, the yielding segment will not squeeze the soft tissues between sternum and clavicle, the segment proximal to sternum and the segment proximal to clavicle forms a staggered arrangement in space. The cross angle of the arrangement is or is close to 90 degree. This makes the segment proximal to sternum and the segment proximal to clavicle fit sternum and clavicle better, further avoids squeezing on soft tissues and organs in postoperative activities, and resolves the effect arising from the rotating and swinging of the sternum locating rod relative to the locating rod junction. In addition, during the operation, after the locating rod junction is installed in place, the clavicle fixation segment can be located in the correct place quickly, and also, the yielding segment can avoid soft tissues between sternum and clavicle, so as to ensure a normal operation.

In the internal fixation plate for sternoclavicular joint stated above, the segment proximal to clavicle and the clavicle fixation segment are integrated into a whole and curved. The segment proximal to sternum is also curved. The structure of this shape can fit sternum and clavicle better and avoid squeezing on soft tissues and organs in postoperative activities.

In the internal fixation plate for sternoclavicular joint stated above, the locating rod junction, the clavicle fixation segment and the transition segment are integrated into a one-piece structure. The segment proximal to sternum, the segment proximal to clavicle and the yielding segment are also integrated into a one-piece structure. The one-piece structure allows the fixation plate a smooth transition without any sharp edges, and avoids scratches.

Compared to the prior art, a preferred embodiment of the internal fixation plate for sternoclavicular joint has the following advantages:

The preferred embodiment of the internal fixation plate for sternoclavicular joint connects the clavicle fixation segment to the sternum locating rod through a movable connection. In patients' postoperative stage, in the ordinary movement of clavicle and sternum, the clavicle fixation segment can rotate and swing relative to the sternum locating rod, so as to prevent the sternum locating rod from scratching and enlarging the bone holes in sternum. This is beneficial to the recovery of the function of patients' sternoclavicular joint, and increases the success rate of the operation.

DETAILED DESCRIPTION OF THE INVENTION

The embodiments of this invention will be described below and the technical solutions of the invention will be further illustrated in connection with the accompanying figures. However, the present invention shall not be limited to these embodiments.

Embodiment I

A preferred Embodiment I of the internal fixation plate for sternoclavicular joint comprises the locating rod junction (1), the clavicle fixation segment (2), the transition segment (3), the screw hole (4), the sternum locating rod (5) and the connector (6).

Figure 1:
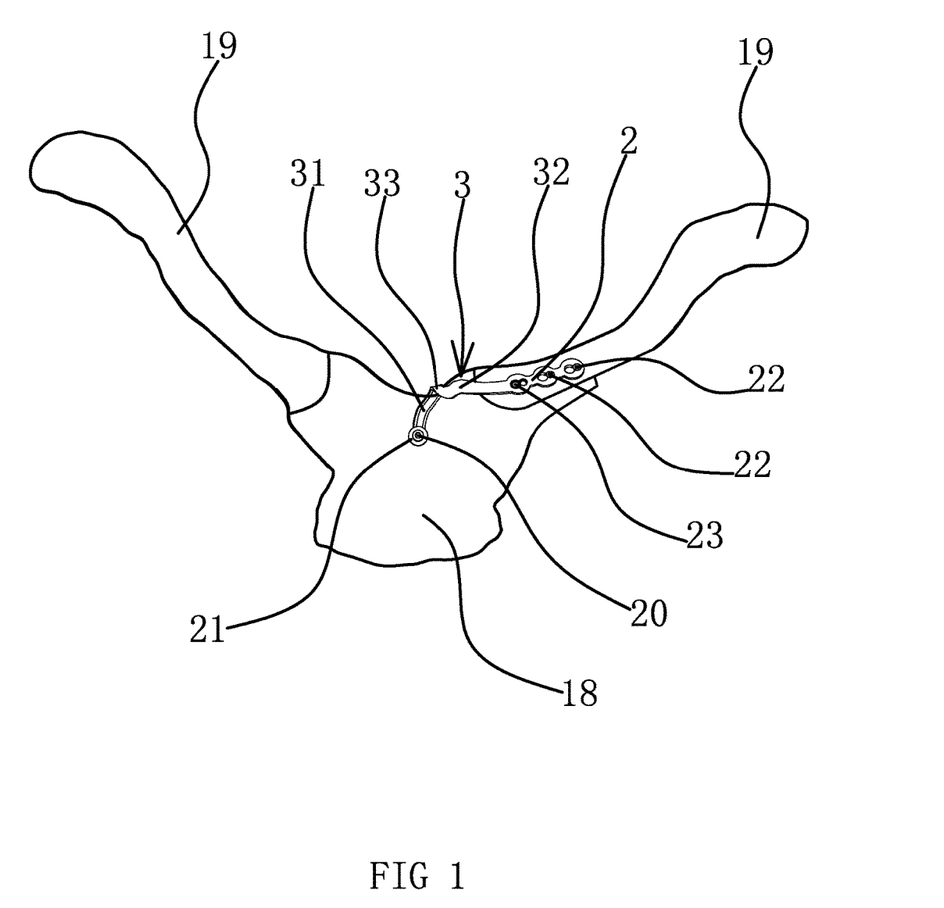
FIG. 1 is the schematic view of one embodiment of the internal fixation plate for sternoclavicular joint in use.
Figure 2:
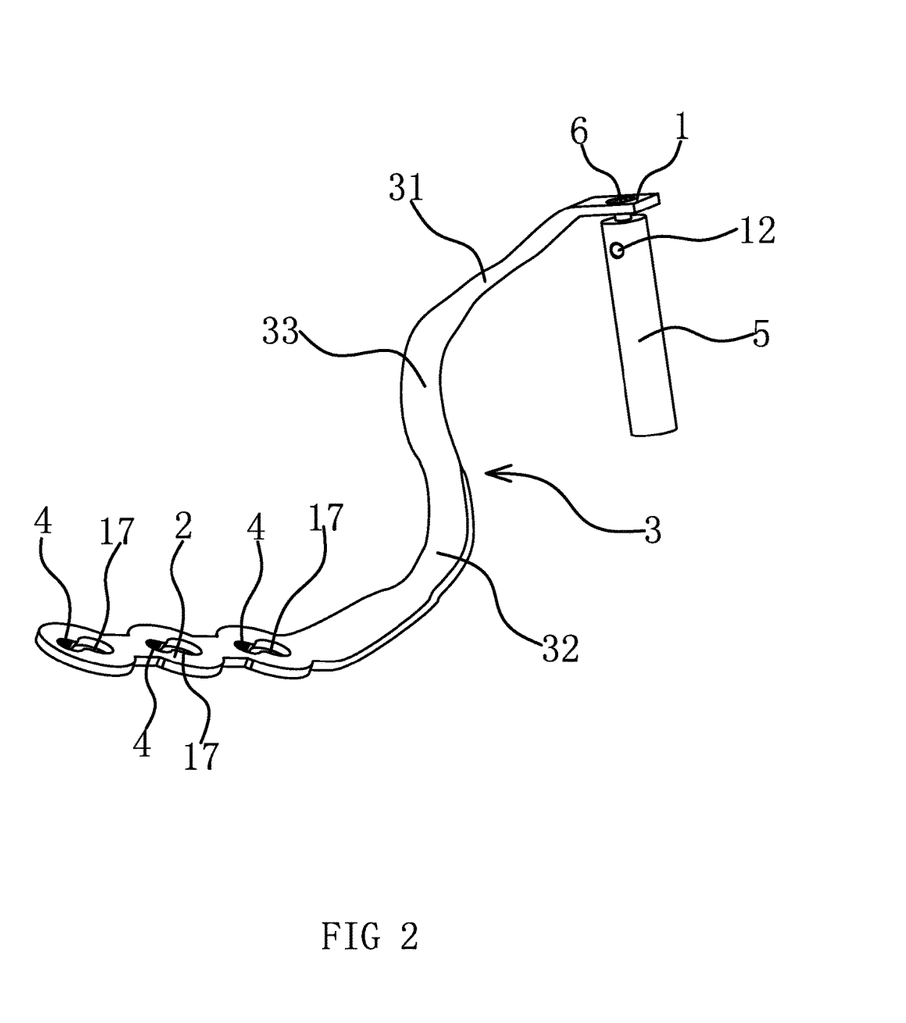
FIG. 2 is the perspective schematic view of one embodiment of the internal fixation plate for sternoclavicular joint.

Specifically, as shown in FIG. 1 and FIG. 2, both the locating rod junction (1) and the clavicle fixation segment (2) have a flat cross section. The locating rod junction (1) and the clavicle fixation segment (2) are not in the same plane, and the transition segment (3) connects in between the locating rod junction (1) and the clavicle fixation segment (2). The locating rod junction (1), the clavicle fixation segment (2) and the transition segment (3) are integrated into a one-piece structure. The transition segment (3) comprises a segment proximal to sternum (31) connecting to the locating rod junction (1), and a segment proximal to clavicle (32) connecting to the clavicle fixation segment (2). Between the segment proximal to sternum (31) and segment proximal to clavicle (32), there is the yielding segment (33). The segment proximal to sternum (31), the segment proximal to clavicle (32) and the yielding segment (33) are integrated into a one-piece structure. The curve of the yielding segment (33) makes the segment proximal to sternum (31) and the segment proximal to clavicle (32) staggered in the fore-and-aft direction. The segment proximal to sternum (31) bends relative to the yielding segment (33) and the segment proximal to clavicle (32) bends relative to the yielding segment (33) in the opposite direction, making the segment proximal to sternum (31) and the segment proximal to clavicle (32) staggered in space. The segment proximal to sternum (31) is curved. The segment proximal to clavicle (32) and the clavicle fixation segment (2) are integrated into a whole and curved.

Figure 3:
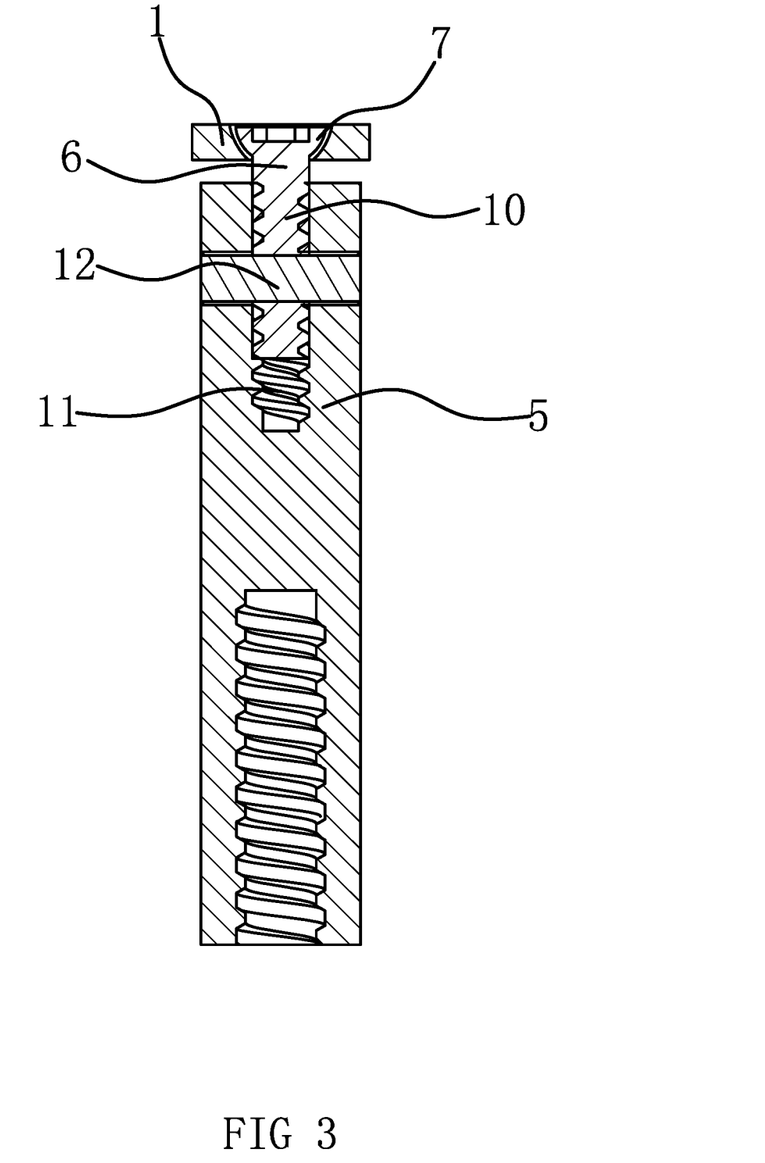
FIG. 3 is the section view of the connection position of the sternum locating rod in the internal fixation plate for sternoclavicular joint in Embodiment I.
Figure 4:
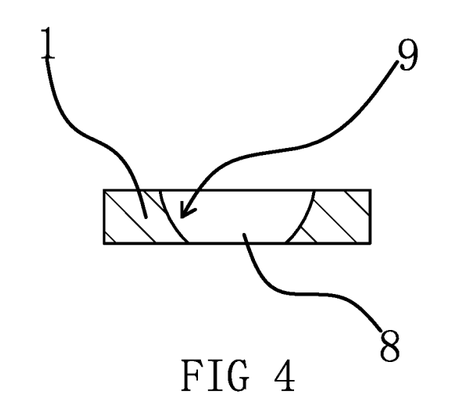
FIG. 4 is the schematic view of the connecting hole in the internal fixation plate for sternoclavicular joint in Embodiment I.
Figure 5:
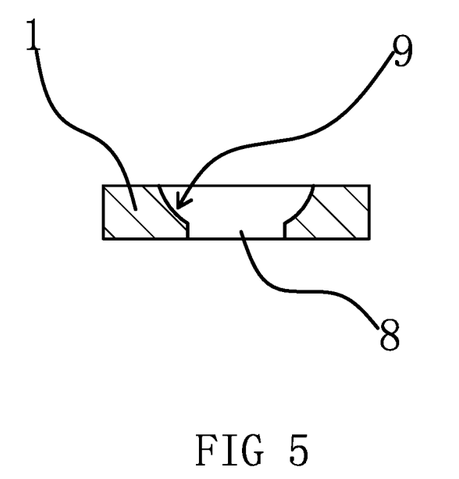
FIG. 5 is the schematic view of another structure of the connecting hole in the internal fixation plate for sternoclavicular joint in Embodiment I.

As shown in FIG. 2 and FIG. 3, the sternum locating rod (5) is connected to the locating rod junction (1) through the connector (6). In this embodiment, the connector (6) is cylindrical. On the end of the connector (6) connecting to the locating rod junction (1), there is a movable head (7), with a greater diameter than the connector (6). On the movable head (7), there is an arc guiding surface (71). There is a connecting hole (8) on the locating rod junction (1) penetrating through the top and bottom surfaces of the locating rod junction (1), and there is a pilot concave (9) inside the connecting hole (8), whose shape matches the guiding surface (71). When the connector (6) passes through the connecting hole (8), the movable head (7) is located inside the connecting hole (8), and the guiding surface (71) of the connector (6) matches the pilot concave (9). In actual machining practices, the pilot concave (9) may extend to the full connecting hole (8), as shown in FIG. 4; or be arranged in the upper part of the connecting hole (8), as shown in FIG. 5, as long as there is a clearance between the guiding surface (71) and the inner wall of the connecting hole (8), which allows the guiding surface (71) to slide along the pilot concave (9). The other end of the connector (6) is threaded connected to the sternum locating rod (5). Such a structure, allows the sternum locating rod (5) to rotate and swing relative to the locating rod junction (1).

As a preferred proposal, there is a threaded segment (10) on the connector (6). There is a threaded hole (11) in the sternum locating rod (5). The connector (6) is located to the sternum locating rod (5) by means of threaded connection, and a locating pin (12) is designed radially in the sternum locating rod (5), which can pass through the threaded segment (10). The sternum locating rod (5) is connected to the connector (6) by means of threaded connection. The distance between the sternum locating rod (5) and locating rod junction (1) can be adjusted, which is convenient for the preoperative preparation and adjustment. The locating pin (12) passes through the threaded segment (10) in the connector (6), and further lock the screw to the sternum locating rod (5). The locating pin (12) and the screw lock with each other, to avoid parts detaching from their locations to cause a medical accident. In actual production and manufacturing practices, the connector (6) and the sternum locating rod (5) may be connected by other means, for example, interference fit, butt fusion, welding and etc. The locating pin (12) may also press against the threaded segment (10).

Figure 13:
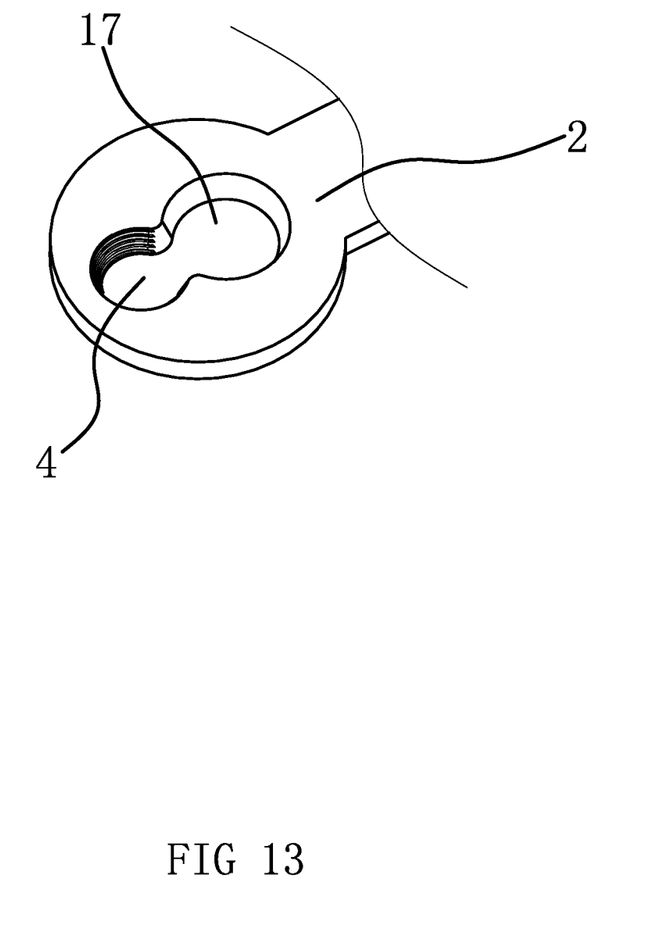
FIG. 13 is the schematic view of the screw hole and locking hole in the internal fixation plate for sternoclavicular joint.

As shown in FIG. 2, the clavicle fixation segment (2) is a long strip structure with a slight arc. Screw holes (4) are designed in the clavicle fixation segment (2). There are several screw holes (4). The screw holes (4) are arranged in the lengthwise direction, and the screw holes (4) have countersinks and internal screw threads. As further preferred, as shown in FIG. 2 and FIG. 13, at the position adjacent to at least one screw hole (4), there is a locking hole (17) designed with a countersink. The locking hole (17) partially overlaps the screw hole (4). The provision of the locking hole (17) will satisfy the requirement for internal fixation with increased pressure, and further enhance the fixation effect between the clavicle fixation segment (2) and clavicle (19).

Figure 14:
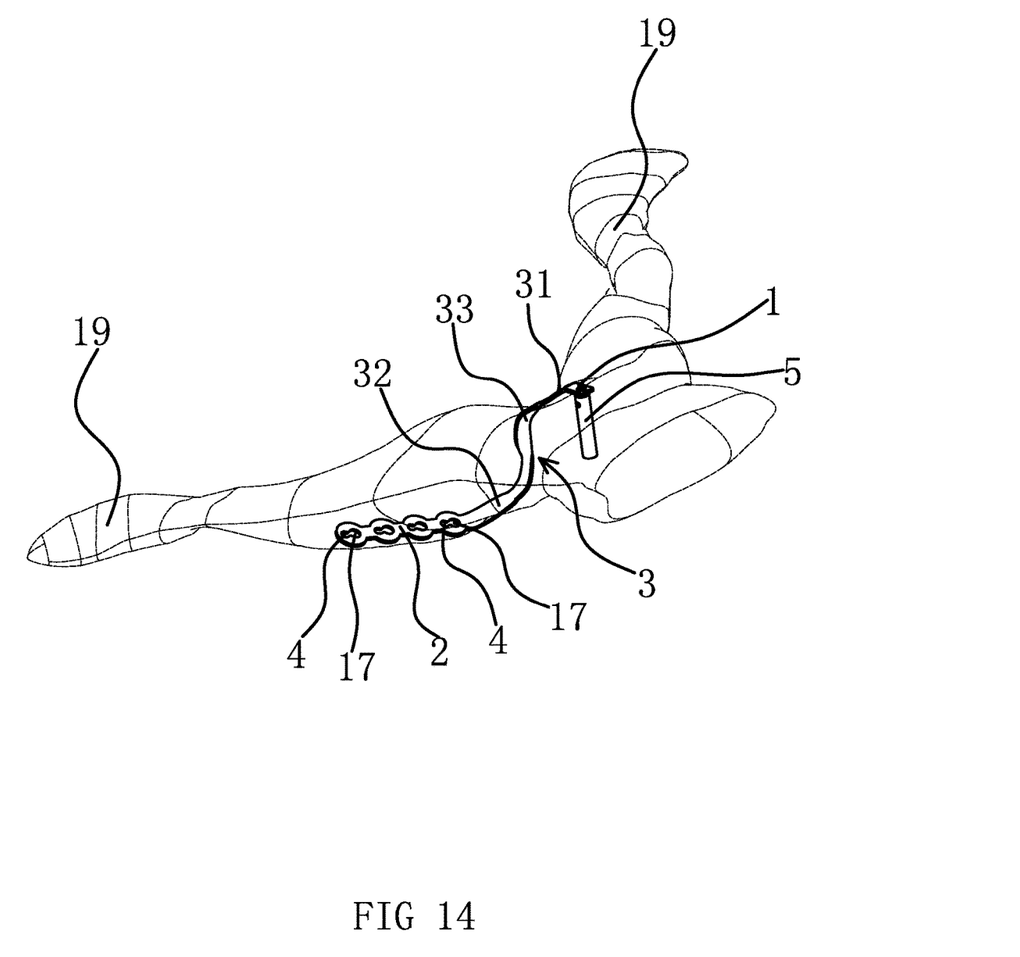
FIG. 14 is the perspective view showing the relative position between sternum plus clavicle and the internal fixation plate for sternoclavicular joint.

In the internal fixation operation with a preferred embodiment of the internal fixation plate of the sternoclavicular joint, as shown in FIG. 1 and FIG. 14, by passing the sternum locating rod (5) through bone holes in sternum from its posterior side and get fixed to sternum, and getting located to sternum (18) with the locating screw (20) and the locating washer (21), by bending the clavicle fixation segment (2) around the posterior sternum and to the anterior clavicle proximal, by, after drilling holes in clavicle, making the cortical bone screw (22) pass through the screw hole (4) and secure the clavicle fixation segment (2) to clavicle (19), and by, as required, applying locking screws (23) to the locking hole (17), the positioning of sternum (18) and clavicle (19) is achieved. During the postoperative recovery, The normal movements of sternum (18) and clavicle (19) allow the guiding surface (71) on the connector (6) to slide relative to the pilot concave (9), and hence mitigates the frictions between the sternum locating rod (5) and the bone holes, so as to prevent the sternum locating rod (5) from scratching the bone holes in sternum (18), the bone holes from enlarging, and the sternum locating rod (5) from moving, and to avoid the fracture in sternum (18), which is beneficial to the postoperative recovery.

Embodiment II

Figure 6:
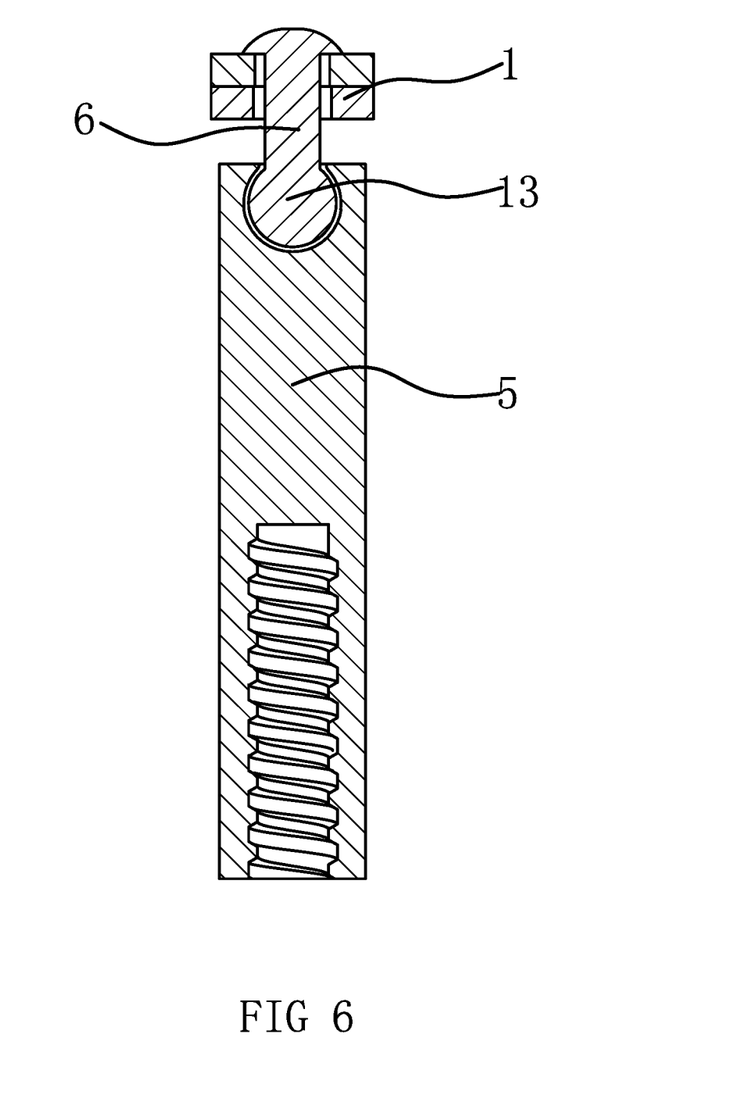
FIG. 6 is the section view of the connection position of the sternum locating rod in the internal fixation plate for sternoclavicular joint in Embodiment II.

In this Embodiment II, as shown in FIG. 6, one end of the connector (6) is fixed to the locating rod junction (1) by means of riveting. The sternum locating rod (5) is connected to the other end of the connector (6), through a spherical connecting structure. In actual machining practices, the connector (6) may also be fixed to the locating rod junction (1) by means of welding, interference fit and etc.

Figure 7:
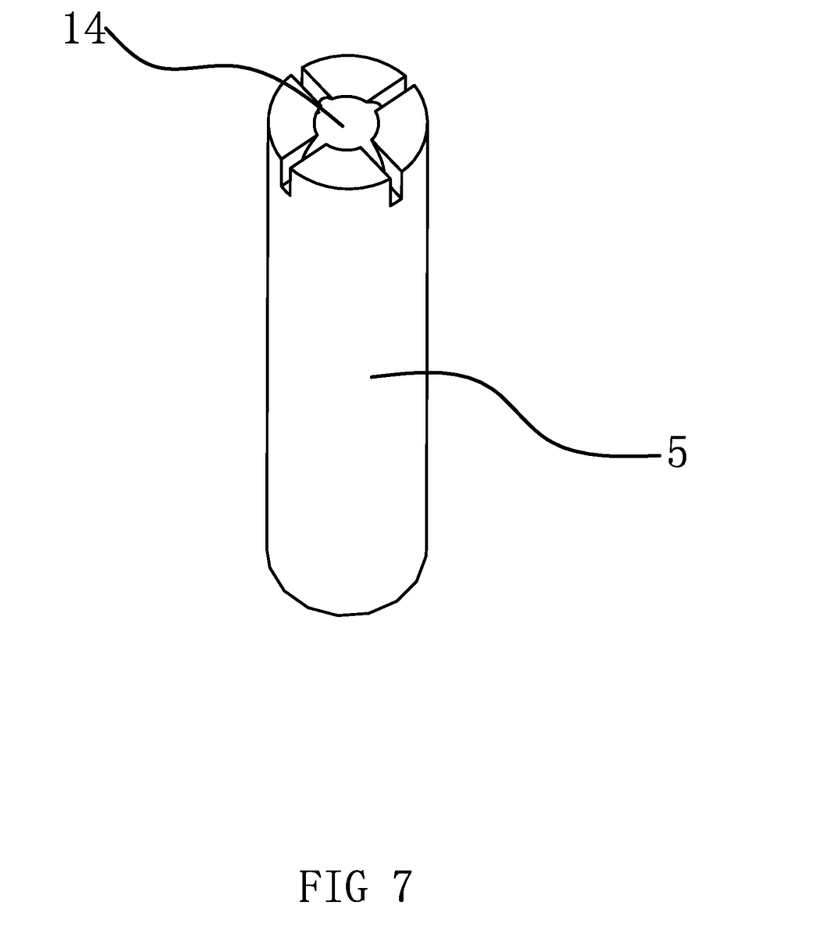
FIG. 7 is the schematic view of the sternum locating rod in the internal fixation plate for sternoclavicular joint in Embodiment II.

In this embodiment, as shown in FIG. 6 and FIG. 7, the spherical connecting structure comprises a ball head (13) on the end of the connector (6) connecting to the sternum locating rod (5). The end of the sternum locating rod (5) is petaloid, and has a spherical hole (14) fitting the ball head (13). Preferably, it has 3 or 4 petals. The ball head (13) is installed into the spherical hole (14) during the production process. The sternum locating rod is preferably made of hard material. In use, the ball head (13) will not detach from the spherical hole (14) because the petaloid structure in the sternum locating rod (5) deforms under forces. In this proposal, during the movements of clavicle (19) and sternum (18), the spherical connecting structure allows the sternum locating rod (5) to rotate and swing relative to the connector (6), which is beneficial to the patient's postoperative recovery. Also, the integrity of the internal fixation plate for sternoclavicular joint is better.

Embodiment III

Figure 8:
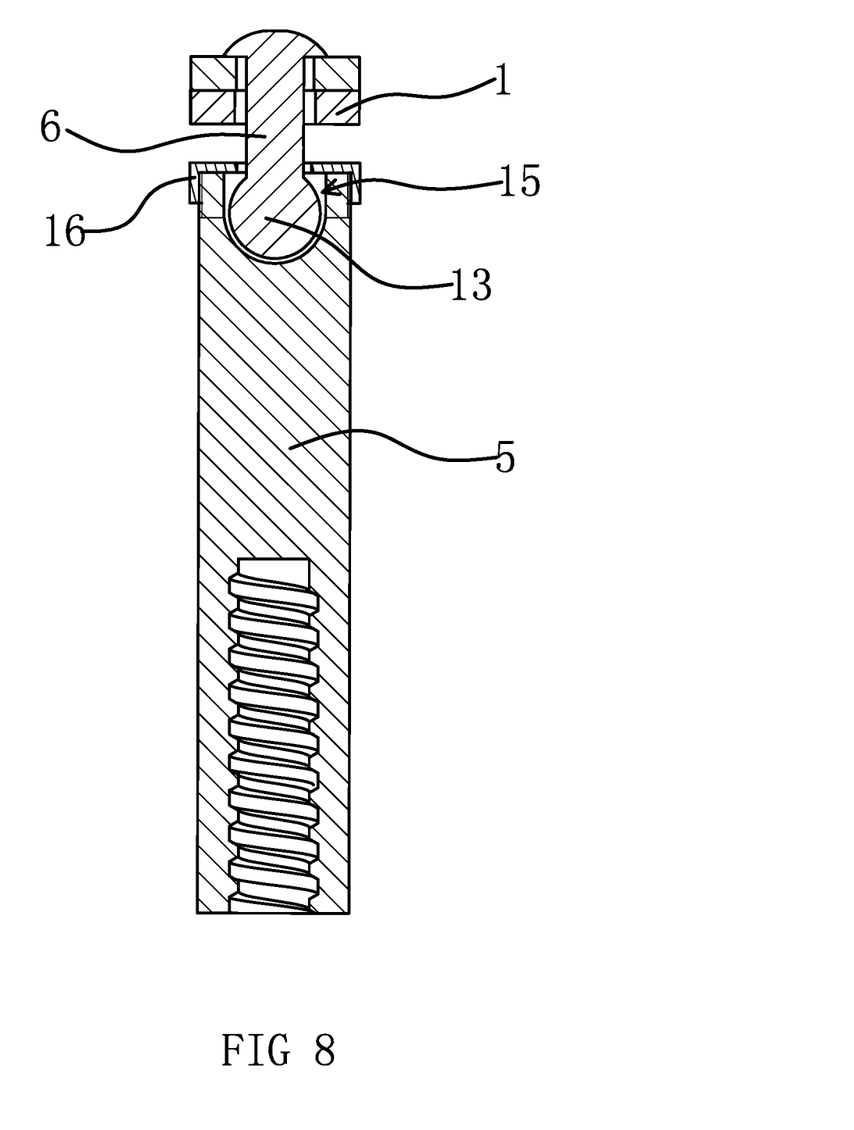
FIG. 8 is the sectional schematic view of the connection position of the sternum locating rod in the internal fixation plate for sternoclavicular joint in Embodiment III.
Figure 9:
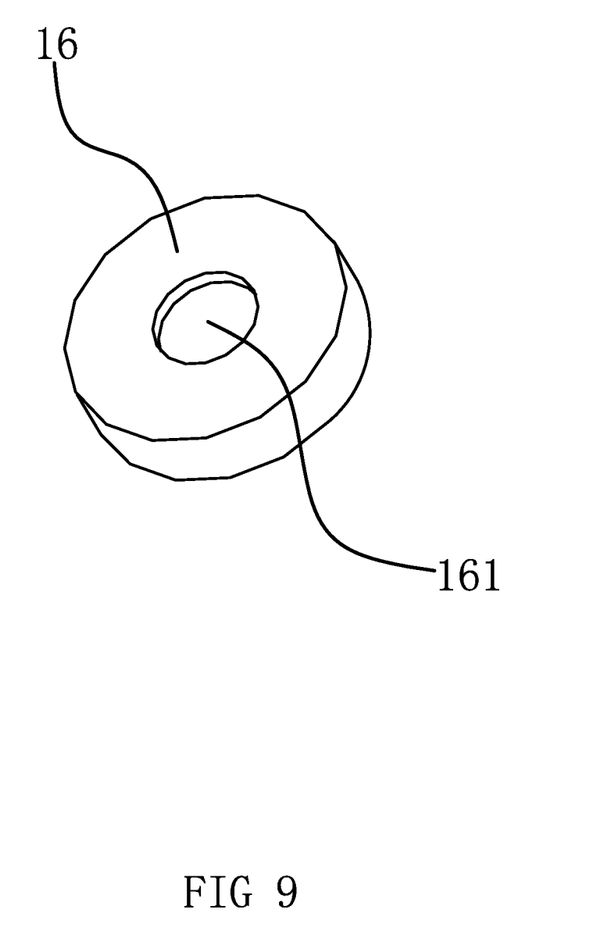
FIG. 9 is the schematic view of the threaded cover in the internal fixation plate for sternoclavicular joint in Embodiment III.

In this Embodiment III, as shown in FIG. 8, the spherical connecting structure comprises a ball head (13) on the end of the connector (6) connecting to the sternum locating rod (5). On the end of the sternum locating rod (5) connecting to the connector (6), there is an enclosing cavity (15). The enclosing cavity (15) has a spherical surface. It is not necessary for the spherical surface to completely enclose the ball head (13). In order to prevent the ball head (13) from detaching from the enclosing cavity (15), a threaded cover (16) is connected to the sternum locating rod (5), by means of threaded connection. As shown in FIG. 9, there is a clearance hole (161) on the threaded cover (16), for the connector (6) to pass through. In order for the ball head (13) to slide inside the enclosing cavity (15), for the sternum locating rod (5) to move relative to the locating rod junction (1), a clearance is kept between the clearance hole (161) and the connector (6). In the preoperative preparation stage, the threaded cover (16) may be unscrewed, after changing the sternum locating rod (5) with one of appropriate dimensions according to the requirements for the operation, the threaded cover (16) can be screwed back tightly, therefore, it is more convenient to use.

Embodiment IV

Figure 10:
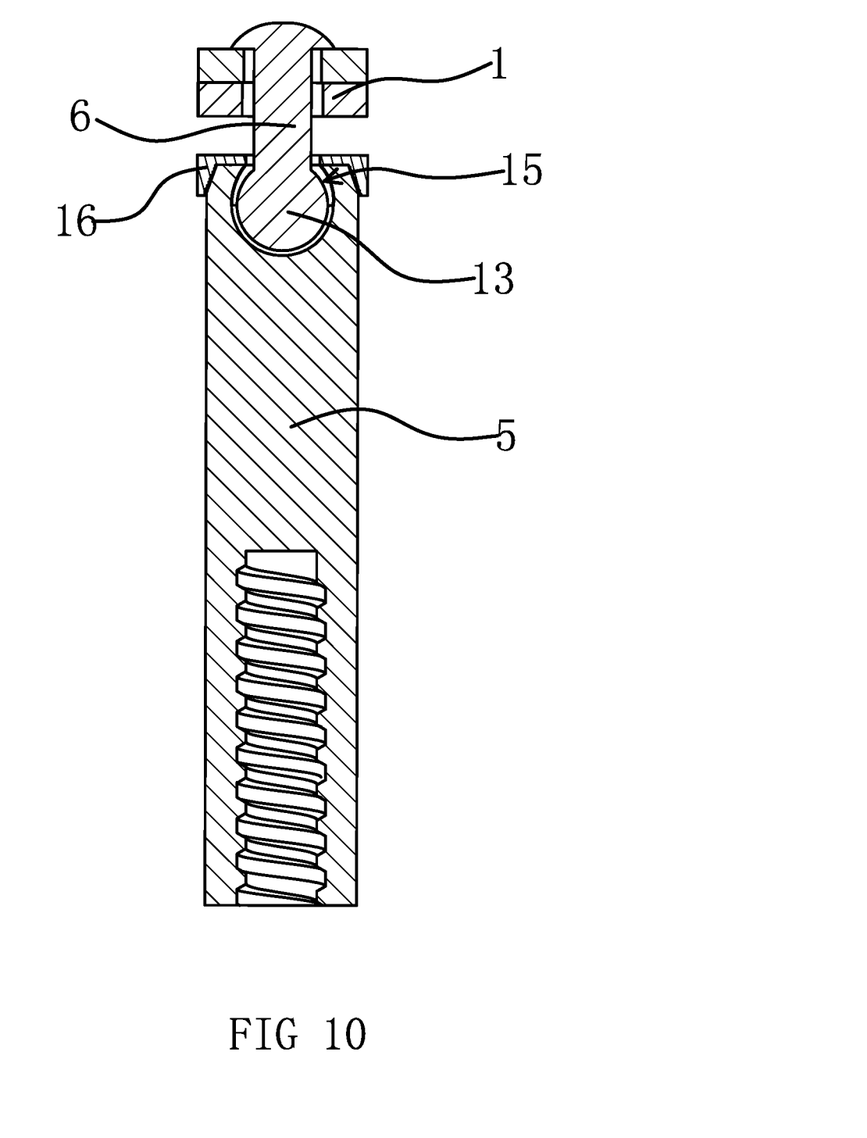
FIG. 10 is the sectional schematic view of the connection position of the sternum locating rod in the internal fixation plate for sternoclavicular joint in Embodiment IV.
Figure 11:
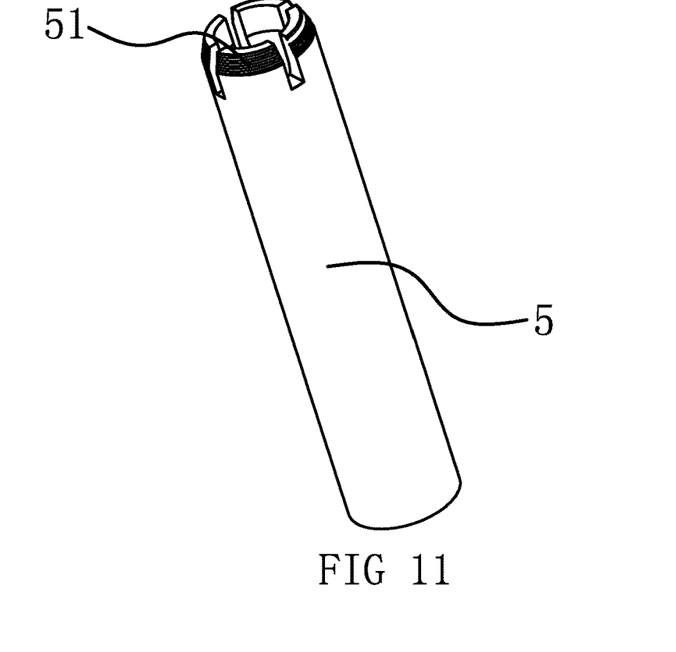
FIG. 11 is the schematic view of the sternum locating rod in the internal fixation plate for sternoclavicular joint in Embodiment IV.
Figure 12:
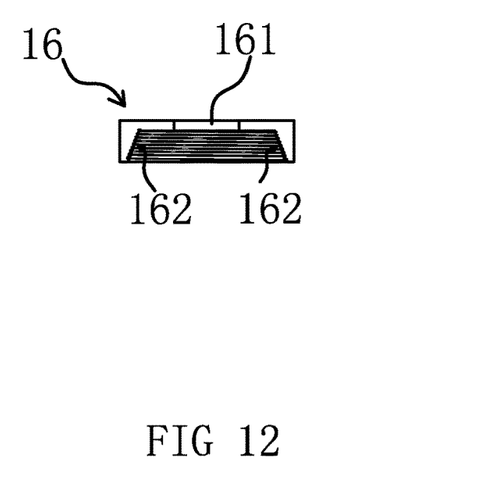
FIG. 12 is the sectional schematic view of the threaded cover in the internal fixation plate for sternoclavicular joint in Embodiment IV.

In this Embodiment IV, as shown in FIG. 10, the enclosing cavity (15) of the sternum locating rod (5) has a spherical dome greater than a hemisphere, and the spherical dome encloses the ball head (13). As shown in FIG. 11 and FIG. 12, at the position of the sternum locating rod (5) corresponding to the enclosing cavity (15), there is a petaloid structure, and the outer wall of the sternum locating rod (5) has a conical surface (51). The inner wall of the threaded cover (16) has a pilot cone (162) matching the conical surface (51). The sternum locating rod (5) is made of material that is easy to deform. By applying forces onto the sternum locating rod (5) or the connector (6), the petaloid structure on the sternum locating rod (5) deforms, and the ball head (13) can be installed into or taken out of the enclosing cavity (15). By screwing the threaded cover (16) tightly to the sternum locating rod (5), the petaloid structure deforms and locks the ball head (13).

The description of the preferred embodiments thereof serves only as an illustration of the spirit of the invention. Those skilled in the art may make various changes, supplements or substitution by adoption of similar methods about the described embodiments therein without departing from the spirit or surpassing the scope of the invention as defined by the appended claims.

Although the terms of Locating Rod Junction (1), Clavicle fixation Segment (2), Transition Segment (3), Segment Proximal to Sternum (31), Segment Proximal to Clavicle (32), Yielding Segment (33), Screw Hole (4), Sternum Locating Rod (5), Conical Surface (51), Connector (6), Movable Head (7), Guiding Surface (71), Connecting Hole (8), Pilot Concave (9), Threaded Segment (10), Threaded Hole (11), Locating Pin (12), Ball Head (13), Spherical Hole (14), Enclosing Cavity (15), Threaded Cover (16), Clearance Hole (161), Pilot Cone (162), Locking Hole (17), Sternum (18), Clavicle (19), Locating Screw (20), Locating Washer (21), Cortical Bone Screw (22) and Locking Screw (23) are often used herein, it does not exclude the possibility to use any other terms. Using such terms is only to describe or explain the nature of the present invention more conveniently. Any additional restrictions are contrary to the spirit of the present invention.

LIST OF REFERENCE NUMERALS

1 Locating Rod Junction
2 Clavicle Fixation Segment
3 Transition Segment
31 Segment Proximal to Sternum
32 Segment Proximal to Clavicle
33 Yielding Segment
4 Screw Hole
5 Sternum Locating Rod
51 Conical Surface
6 Connector
7 Movable Head
71 Guiding Surface
8 Connecting Hole
9 Pilot Concave
10 Threaded Segment
11 Threaded Hole
12 Locating Pin
13 Ball Head
14 Spherical Hole
15 Enclosing Cavity
16 Threaded Cover
161 Clearance Hole
162 Pilot Cone
17 Locking Hole
18 Sternum
19 Clavicle
20 Locating Screw
21 Locating Washer
22 Cortical Bone Screw
23 Locking Screw

What is claimed is:

1. An internal fixation plate for a sternoclavicular joint comprising:
  a locating rod junction (1) and a clavicle fixation segment (2), both with flat cross sections, the locating rod junction (1) and the clavicle fixation segment (2) are not in a same plane;
  a transition segment (3) connects in between the locating rod junction (1) and the clavicle fixation segment (2); and
  screw holes (4) are designed in the clavicle fixation segment (2);
  wherein the clavicle fixation segment (2) is of a long strip; and
  wherein the locating rod junction (1) is movably connected to a columnar sternum locating rod (5), through a connector (6), which allows the sternum locating rod (5) to rotate or swing relative to the locating rod junction (1).

2. The internal fixation plate for a sternoclavicular joint as claimed in claim 1, wherein on an end of the connector (6) connecting to the locating rod junction (1), there is a movable head (7), with a greater diameter than the connector (6);
  wherein there is a circular arc shaped guiding surface (71) on the movable head (7);
  wherein there is a connecting hole (8) on the locating rod junction (1) penetrating through top and bottom surfaces of the locating rod junction (1), and there is a pilot concave (9) inside the connecting hole (8), whose shape matches the guiding surface (71);
  wherein the guiding surface (71) is capable of pressing against the pilot concave (9), when the connector (6) passes through the connecting hole (8);
  wherein there is a clearance between the connector (6) and an inner wall of the connecting hole (8); and
  wherein an other end of the connector (6) is fixed to the sternum locating rod (5).

3. The internal fixation plate for a sternoclavicular joint as claimed in claim 2, wherein there is a threaded segment (10) on the connector (6);
  wherein on the sternum locating rod (5), there is a threaded hole (11) fitting the threaded segment (10); and
  wherein on the sternum locating rod (5), there is a locating pin (12) designed in a radial direction, which is capable of locking the connector (6) onto the sternum locating rod (5).

4. The internal fixation plate for a sternoclavicular joint as claimed in claim 1, wherein one end of the connector (6) is fixed to the locating rod junction (1); and
  wherein the sternum locating rod (5) is connected to an other end of the connector (6), through a spherical connecting structure.

5. The internal fixation plate for a sternoclavicular joint as claimed in claim 4, wherein the spherical connecting structure comprises a ball head (13) on an end of the connector (6) connecting to the sternum locating rod (5);
  wherein an end of the sternum locating rod (5) is petaloid, and has a spherical hole (14) fitting the ball head (13); and
  wherein the ball head (13) is embedded into the spherical hole (14).

6. The internal fixation plate for a sternoclavicular joint as claimed in claim 4, wherein the spherical connecting structure comprises a ball head (13) on an end of the connector (6) connecting to the sternum locating rod (5);
  wherein on an end of the sternum locating rod (5) connecting to the connector (6), there is a spherical enclosing cavity (15);
  wherein a threaded cover (16) is also screwed onto the sternum locating rod (5), locating the ball head (13) inside the enclosing cavity (15);
  wherein there is a clearance hole (161) on the threaded cover (16), for the connector (6) to pass through; and
  wherein there is a clearance between the clearance hole (161) and the connector (6).

7. The internal fixation plate for a sternoclavicular joint as claimed in claim 6, wherein at a position of the sternum locating rod (5) corresponding to the enclosing cavity (15), there is a petaloid structure, and an outer wall of the sternum locating rod (15) has a conical surface (51); and
  wherein an inner wall of the threaded cover (16) has a pilot cone (162) matching the conical surface (51).

8. The internal fixation plate for a sternoclavicular joint as claimed in claim 1, wherein there are several screw holes (4); and
  wherein the screw holes (4) are arranged in a lengthwise direction of the clavicle fixation segment (2), and the screw holes (4) have countersinks and internal screw threads.

9. The internal fixation plate for a sternoclavicular joint as claimed in claim 8, wherein at a position adjacent to at least one screw hole (4), there is a locking hole (17) designed with a countersink; and wherein the locking hole (17) partially overlaps the screw hole (4).

10. The internal fixation plate for a sternoclavicular joint as claimed in claim 1, wherein the transition segment (3) comprises a segment proximal to a sternum (31) connecting to the locating rod junction (1), and a segment proximal to a clavicle (32) connecting to the clavicle fixation segment (2);
   wherein between the segment proximal to the sternum (31) and the segment proximal to the clavicle (32), there is a yielding segment (33);
   wherein a curve of the yielding segment (33) makes the segment proximal to the sternum (31) and the segment proximal to the clavicle (32) staggered in a fore-and-aft direction; and
   wherein the segment proximal to the sternum (31) bends relative to the yielding segment (33) and the segment proximal to the clavicle (32) bends relative to the yielding segment (33) in an opposite direction, making the segment proximal to the sternum (31) and the segment proximal to the clavicle (32) staggered in space.

11. The internal fixation plate for a sternoclavicular joint as claimed in claim 10, wherein the segment proximal to the clavicle (32) and the clavicle fixation segment (2) are curved.

12. The internal fixation plate for a sternoclavicular joint as claimed in claim 11, wherein the segment proximal to the sternum (31) is also curved.

13. The internal fixation plate for a sternoclavicular joint as claimed in claim 12, wherein the locating rod junction (1), the clavicle fixation segment (2) and the transition segment (3) are integrated into a one-piece structure; and
   wherein the segment proximal to the sternum (31), the segment proximal to the clavicle (32) and the yielding segment (33) are also integrated into a one-piece structure.

14. The internal fixation plate for a sternoclavicular joint as claimed in claim 2 wherein there are several screw holes (4); and
   wherein the screw holes (4) are arranged in a lengthwise direction of the clavicle fixation segment (2), and the screw holes (4) have countersinks and internal screw threads.

15. The internal fixation plate for a sternoclavicular joint as claimed in claim 3 wherein there are several screw holes (4); and
   wherein the screw holes (4) are arranged in a lengthwise direction of the clavicle fixation segment (2), and the screw holes (4) have countersinks and internal screw threads.

16. The internal fixation plate for a sternoclavicular joint as claimed in claim 4 wherein there are several screw holes (4); and
   wherein the screw holes (4) are arranged in a lengthwise direction of the clavicle fixation segment (2), and the screw holes (4) have countersinks and internal screw threads.

17. The internal fixation plate for a sternoclavicular joint as claimed in claim 5 wherein there are several screw holes (4); and
   wherein the screw holes (4) are arranged in a lengthwise direction of the clavicle fixation segment (2), and the screw holes (4) have countersinks and internal screw threads.

18. The internal fixation plate for a sternoclavicular joint as claimed in claim 6 wherein there are several screw holes (4); and
   wherein the screw holes (4) are arranged in a lengthwise direction of the clavicle fixation segment (2), and the screw holes (4) have countersinks and internal screw threads.

19. The internal fixation plate for a sternoclavicular joint as claimed in claim 7 wherein there are several screw holes (4); and
   wherein the screw holes (4) are arranged in a lengthwise direction of the clavicle fixation segment (2), and the screw holes (4) have countersinks and internal screw threads.

20. The internal fixation plate for a sternoclavicular joint as claimed in claim 2 wherein the transition segment (3) comprises a segment proximal to a sternum (31) connecting to the locating rod junction (1), and a segment proximal to a clavicle (32) connecting to the clavicle fixation segment (2);
   wherein between the segment proximal to the sternum (31) and the segment proximal to the clavicle (32), there is a yielding segment (33);
   wherein a curve of the yielding segment (33) makes the segment proximal to the sternum (31) and the segment proximal to the clavicle (32) staggered in a fore-and-aft direction; and
   wherein the segment proximal to the sternum (31) bends relative to the yielding segment (33) and the segment proximal to the clavicle (32) bends relative to the yielding segment (33) in an opposite direction, making the segment proximal to the sternum (31) and the segment proximal to the clavicle (32) staggered in space.

\* \* \* \* \*